United States Patent
Holland et al.

(10) Patent No.: US 12,012,386 B2
(45) Date of Patent: Jun. 18, 2024

(54) OLAPARIB OXALIC ACID COCRYSTALS AND THEIR PHARMACEUTICAL USE

(71) Applicant: NUFORMIX TECHNOLOGIES LIMITED, London (GB)

(72) Inventors: Joanne Holland, Cambridge (GB); Alex Eberlin, Cambridge (GB); Christopher Frampton, Stowmarket (GB)

(73) Assignee: NUFORMIX TECHNOLOGIES LIMITED, London (GB)

( * ) Notice: Subject to any disclaimer, the term of this patent is extended or adjusted under 35 U.S.C. 154(b) by 0 days.

(21) Appl. No.: 18/245,624

(22) PCT Filed: Sep. 14, 2021

(86) PCT No.: PCT/IB2021/000617
§ 371 (c)(1),
(2) Date: Mar. 16, 2023

(87) PCT Pub. No.: WO2022/058785
PCT Pub. Date: Mar. 24, 2022

(65) Prior Publication Data
US 2023/0322686 A1   Oct. 12, 2023

Related U.S. Application Data

(60) Provisional application No. 63/079,018, filed on Sep. 16, 2020.

(51) Int. Cl.
C07D 237/32  (2006.01)

(52) U.S. Cl.
CPC ........ C07D 237/32 (2013.01); *C07B 2200/13* (2013.01)

(58) Field of Classification Search
CPC .......................... C07D 237/32; C07B 2200/13
See application file for complete search history.

(56) References Cited

FOREIGN PATENT DOCUMENTS

| CN | 111825621 A | 10/2020 | |
|---|---|---|---|
| WO | 2008/047082 A2 | 4/2008 | |
| WO | WO-2008047082 A2 * | 4/2008 | ........... A61K 31/502 |
| WO | 2016/165650 A1 | 10/2016 | |
| WO | WO-2016165650 A1 * | 10/2016 | |
| WO | 2017/191562 A1 | 11/2017 | |
| WO | 2021/044437 A1 | 3/2021 | |

OTHER PUBLICATIONS

Liu et al. European Journal of Pharmaceutic and Biopharmaceutics 154, 2020, 62-73, available online Jul. 2020 (Year: 2020).*
Kaupp (Solvent-Less Organic Synthesis. In Kirk-Othermer Encyclopedia of Chemical Technology (Ed.) 2012 (Year: 2012).*
Margaret et al. Int. J. Pharmacol. ISSN: 2581-3080, vol. 4, Iss 1, Published Mar. 2020 (Year: 2023).*
Antonarakis. Nature Reviews Clinical Oncology, 17, 455-456, Published May 2020 (Year: 2020).*
Zheng. Biomedicine and Pharmacotherapy 123 (2020) 109661 (Year: 2020).*
Devogelaer, Angew. Chem. Int. Ed. 2020, 59, 21711-21718 (Year: 2020).*
Issa, Crystal Growth &Design, vol. 9, No. 1, 2009 (Year: 2009).*
Ngilirabanga, Nano Select 2021;2:512-526 (Year: 2021).*
International Preliminary Report on Patentability of PCT International Application No. PCT/IB2021/000617 filed Sep. 14, 2021, dated Mar. 21, 2023.
International Search Report and Written Opinion of PCT International Application No. PCT/IB2021/000617 filed Sep. 14, 2021, dated Jan. 19, 2022.
Bavishi et al. "Spring and parachute: How cocrystals enhance solubility", Progress in Crystal Growth and Characterization of Materials, vol. 62, No. 3, Aug. 4, 2016 (Aug. 4, 2016) pp. 1-8.

* cited by examiner

*Primary Examiner* — Susanna Moore
*Assistant Examiner* — Luisalberto Gonzalez
(74) *Attorney, Agent, or Firm* — RAPHAEL BELLUM PLLC

(57) ABSTRACT

The invention relates to new olaparib oxalic acid cocrystals. The olaparib oxalic acid cocrystals vary in ratio from 1:1 to 2:3 olaparib:oxalic acid. In particular, the invention relates to a 2:3 olaparib oxalic acid cocrystal, a 1:1 olaparib oxalic acid cocrystal, and a 2:1 olaparib oxalic acid cocrystal. The invention also relates to pharmaceutical compositions containing an olaparib oxalic acid cocrystal of the invention and a pharmaceutically acceptable carrier. The olaparib oxalic acid cocrystals of the invention Got may be useful for the treatment of diseases that benefit from inhibition of poly (ADP-ribose) polymerase (PARP). These include cancer, fibrosis, inflammatory conditions (e.g. asthma, colitis, arthritis), neurological diseases (e.g. neurodegeneration, neurotrauma, stroke), cardiovascular conditions, ophthalmic degenerative diseases, vascular diseases (e.g. diabetic complications, atherosclerosis), and various forms of critical illness (e.g. septic shock, ALI, acute liver failure).

12 Claims, 12 Drawing Sheets

OLAPARIB OXALIC ACID COCRYSTALS AND THEIR PHARMACEUTICAL USE

CROSS-REFERENCE TO RELATED APPLICATIONS

This application claims priority to U.S. Provisional Application No. 63/079,018 filed on Sep. 16, 2020, the disclosure of which is incorporated by reference.

TECHNICAL FIELD

This disclosure relates to olaparib oxalic acid cocrystals, therapeutic uses of the cocrystals and pharmaceutical compositions containing them.

BACKGROUND

Olaparib, (4-[(3-{[4-(cyclopropylcarbonyl)piperazin-1-yl]carbonyl}-4-fluorophenyl)methyl]phthalazin-1(2H)-one, shown below), is an inhibitor of the enzyme poly (ADP-ribose) polymerase (PARP). Its synthesis was first described in WO2004080976.

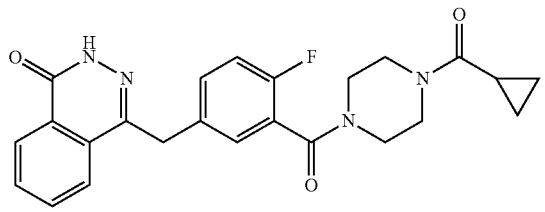 [SMILES: O=C(c1cc(Cc2n[nH]c(=O)c3ccccc23)ccc1F)N1CCN(C(=O)C2CC2)CC1]

Olaparib is currently marketed by AstraZeneca, under the Lynparza® brand name for the treatment of adults with suspected deleterious germline or somatic BRCA gene mutated ovarian, breast, or pancreatic cancer, or for suspected deleterious germline or somatic HRR gene mutated prostate cancer.

As described by the European Medicines Agency CHM P assessment report (EMA/CHMP/789139/2014) olaparib is classified by the Biopharmaceutical Classification System (BCS) as being a class 4 drug meaning it has both low solubility and low permeability. To enable sufficient efficacy, it is therefore critical to find forms of olaparib with the highest possible solubility and bioavailability. Olaparib exists in multiple polymorphic forms, as well as solvated and hydrated forms, which have been disclosed, for example, in WO2008/04708 (Form A), WO2009/050469 (Form L), WO2010/041051, WO2017/123156, and WO2017/40283. The original marketed formulation contained polymorph A which has pH independent aqueous solubility of ~0.1 mg/ml. As the polymorphic crystalline forms of olaparib have such low solubility, a solubility enhancing formulation was required to achieve sufficient bioavailability. The original marketed formulation was a capsule, where olaparib Form A was micronised and formulated as a crystalline solid dispersion using the semi-solid Lauroyl macrogolglyceride (LMG) matrix. This formulation improved the bioavailability of pure crystalline olaparib, however, due to the amount of LMG needed in the formulation only 50 mg capsules were possible. Clinical trials showed the efficacious dose of olaparib to be 400 mg twice daily resulting in patients requiring 16 capsules per day. It was also found that different polymorphic forms of olaparib can arise even when using the same solvent or solvent mixture. For example, WO2009/050469 and WO2008/04708 demonstrate that both ethanol/water and methanol/water can afford both Form A and Form L (both anhydrous forms) whereas water alone produces olaparib hydrate (Form H). Also, different solvents can lead to different solvated forms and mixed solvents can lead to mixed solvates of differing ratios (WO2017/40283). It is therefore difficult to control the precise form of olaparib that is produced using a specific method. In 2018 AstraZeneca had to recall a batch of olaparib capsules as they were found to contain levels of polymorph L above the specified limit. They also recalled several other batches for fear that amounts of Form L may increase during the shelf life of the capsules. There is therefore a need for new crystalline forms of olaparib that do not exist in multiple polymorphic forms and that do not convert form on storage or produce solvated or hydrated forms.

More recently a new tablet formulation has been developed to overcome some of these limitations. The tablet formulation contains an amorphous solid dispersion of olaparib in a matrix with copovidone polymer, formed using a melt extrusion method. This new tablet formulation showed higher bioavailability, resulting in the daily dose of olaparib being lowered from 800 mg to 600 mg. Use of an amorphous form of olaparib also overcame the issue of polymorph conversion, although amorphous forms being metastable are always less stable than crystalline forms in terms of storage, therefore requiring large amounts of stabiliser to maintain the amorphous form and always carry the risk of re-crystallisation on storage. Also, as the polymer used in the table matrix is hygroscopic the tablet formulation requires protective packaging to prevent moisture uptake. It would be preferable to find an alternative crystalline form of olaparib that could provide higher solubility, like an amorphous form, but without the inherent poor stability of amorphous forms and without the need for a stabilising agent.

Over recent years it has been found that the enzyme PARP plays a key role in multiple non-oncological diseases (C. Szabo et al. *B. J. Pharm.* (2018) 175: 1932-222). PARP has been shown to be associated with pulmonary inflammatory diseases such as asthma, COPD, and acute lung injury as well as other inflammatory conditions such as arthritis and colitis. It has also been found to be a major contributing factor in neurodegenerative diseases such as Parkinson's and Alzheimer's diseases, in cardiovascular conditions such as myocardial ischemia/reperfusion injury, various forms of heart failure, cardiomyopathies, circulatory shock, cardiovascular aging, diabetic cardiovascular complications, myocardial hypertrophy, atherosclerosis, vascular remodelling following injury and atherosclerosis. PARP has been implicated in several ophthalmic diseases such as retinal degeneration, retinal or optic nerve disease and glaucoma (U.S. Pat. No. 6,444,676). PARP has been shown to be a key mediating factor in the progression of multiple types of fibrosis including lung, cardiac, liver, and renal fibrosis. This would suggest that olaparib could be used to treat numerous non-oncological conditions.

However, oral olaparib has multiple tolerability side effects that can often be severe including nausea, vomiting, fatigue, and anaemia. Development of alternative delivery methods that would allow local delivery of olaparib to enable treatment of disease with minimal systemic exposure could allow olaparib to be repurposed into new diseases with lower risk of side effects, potentially increasing patient compliance. Also given the wide range of diseases for which olaparib could have a potential therapeutic benefit, as well as the different patient types and specific areas of the body requiring treatment, it is anticipated that patients would benefit from having multiple delivery methods for the administration of olaparib so as to best suit the patient's needs. The pharmaceutical compositions could include, for example, an inhalable composition, an ophthalmic composition, a topical composition, or a transdermal composition. For example, an inhaled formulation could allow treatment of lung diseases such as lung fibrosis, asthma, COPD, and ALI without the side effects of oral delivery. However, amorphous drug forms that require large amounts of stabilising polymer and are hygroscopic, or crystalline forms subject to polymorph instability, are not suitable for inhaled delivery. Alternatively, the low solubility of the known crystalline forms of olaparib would not enable ophthalmic or dermal formulation. There is, therefore, a need for new crystalline forms of olaparib with both good stability and increased solubility to enable alternative formulations of olaparib to treat novel PARP mediated diseases.

The most common alternative crystalline form used to improve the solubility of a low solubility drug is a pharmaceutically acceptable salt. A crystalline salt is formed when the drug and a second component are crystallised together to form a two-component crystalline complex, held together through ionic bonding, with proton transfer occurring between the two components. A drug salt will often have superior physical properties compared to the pure crystalline drug. However, olaparib is non-ionisable, so it cannot form salts. For non-ionisable drugs formation of a cocrystal is an alternative two-component crystalline complex where the drug and a second component are held together through non-ionic bonds such as hydrogen bonds or Van der Waals bonds with no proton exchange occurring between the two components. The second component in a cocrystal is termed a 'coformer'. Drug cocrystals have unique crystalline structures with distinct crystallographic and spectroscopic properties compared to the drug and coformer individually. These multi-component assemblies are continuing to excite and find usefulness, particularly within the pharmaceutical field, as drug cocrystals often possess more favourable pharmaceutical properties compared to the pure drug, often making them more suitable for new drug delivery options not possible with either the pure crystalline drug or its amorphous form. This is because a cocrystal form may have improved dissolution or solubility properties or advantageous storage stability, melting point, hygroscopicity, etc. For a pharmaceutical cocrystal of olaparib to be used as an alternative marketed form of olaparib it is important that the coformer used is 'inactive' and that it possesses regulatory acceptability for use in a pharmaceutical formulation. A 1:1 olaparib urea cocrystal has previously been disclosed in CN 105753789. However, as this patent only discloses one cocrystal of olaparib, there remains, therefore, a need for other pharmaceutically acceptable olaparib cocrystals with an even greater improvement in dissolution rate and lower hygroscopicity. A 1:1 olaparib fumaric acid cocrystal and a 1:1 olaparib 3,5-dihydroxybenzoic acid cocrystal have previously been disclosed in WO 2021/044437; a 1:1 olaparib maleic acid cocrystal has previously been disclosed in CN 111689905; and a 1:1 olaparib malonic acid cocrystal has previously been disclosed in CN 111825621. However, these cocrystals could not be repeated with the methods disclosed therein.

SUMMARY

The invention relates to new olaparib oxalic acid cocrystals. The olaparib oxalic acid cocrystals vary in ratio from 1:1 to 2:3 olaparib:oxalic acid. In particular, the invention relates to a 2:3 olaparib oxalic acid cocrystal, a 1:1 olaparib oxalic acid cocrystal, and a 2:1 olaparib oxalic acid cocrystal. The invention also relates to pharmaceutical compositions containing an olaparib oxalic acid cocrystal of the invention and a pharmaceutically acceptable carrier. The olaparib oxalic acid cocrystals of the invention may be used in the same way as olaparib. Olaparib is useful in treating diseases that benefit from inhibition of poly (ADP-ribose) polymerase (PARP). These include cancer, fibrosis, inflammatory conditions (e.g. asthma, colitis, arthritis), neurological diseases (e.g. neurodegeneration, neurotrauma, stroke), cardiovascular conditions, ophthalmic degenerative diseases, vascular diseases (e.g. diabetic complications, atherosclerosis), and various forms of critical illness (e.g. septic shock, ALI, acute liver failure). The olaparib oxalic acid cocrystals of the invention may, therefore, be useful for the treatment of such diseases, disorders, and conditions.

DETAILED DESCRIPTION

Figure 1:
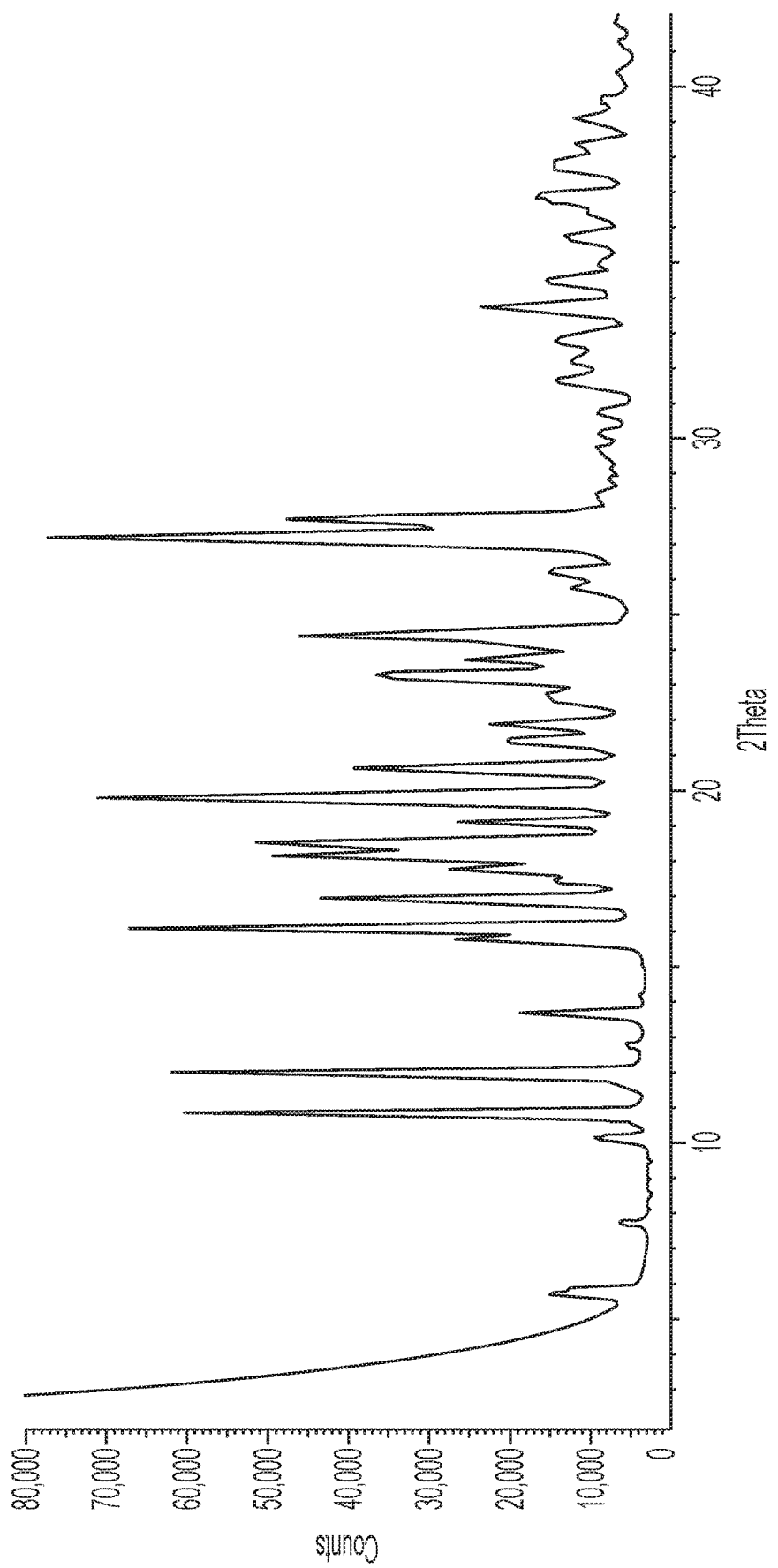
FIG. 1 shows an XRPD diagram of the 2:3 olaparib oxalic acid cocrystal.

The invention relates to new olaparib oxalic acid cocrystals. The olaparib oxalic acid cocrystals vary in ratio from 1:1 to 2:3 olaparib:oxalic acid. In particular, the invention relates to a 2:3 olaparib oxalic acid cocrystal, a 1:1 olaparib oxalic acid cocrystal, and a 2:1 olaparib oxalic acid cocrystal. These olaparib oxalic acid cocrystals of the invention, their preparation and their characterization are described in the examples below and shown in the figures. The invention relates to pharmaceutical compositions containing a therapeutically effective amount of an olaparib oxalic acid cocrystal of the invention and a pharmaceutically acceptable carrier. The invention also relates to methods of treatment for the diseases, disorders and conditions described herein and the use of a therapeutically effective amount of an olaparib oxalic acid cocrystal of the invention, or a pharmaceutical composition containing it, for that treatment. The invention further provides the use of an olaparib oxalic acid cocrystal of the invention in the manufacture of a medicament for use in the treatment of the diseases, disorders, and conditions described herein.

Therapeutic Uses of Olaparib Oxalic Acid Cocrystals

As discussed above olaparib is known in the art to be useful in the treatment of various diseases, disorders, and conditions. The olaparib oxalic acid cocrystals of the invention, 2:3 olaparib oxalic acid cocrystal, 1:1 olaparib oxalic acid cocrystal, and 2:1 olaparib oxalic acid cocrystal, and pharmaceutical compositions containing them may then also be used to treat such diseases, disorders, and conditions. The diseases, disorders, or conditions which may treated with an olaparib oxalic acid cocrystal of the invention include, but are not limited to: cancer, fibrosis, inflammatory conditions (e.g. asthma, colitis, arthritis), neurological diseases (e.g. neurodegeneration, neurotrauma, stroke), cardiovascular conditions, ophthalmic degenerative diseases, vascular diseases (e.g. diabetic complications, atherosclerosis), and various forms of critical illness (e.g. septic shock, ALI, acute liver failure).

Accordingly, the invention relates to the method of treating such a disease, disorder, or condition comprising the step of administering to a patient in need thereof a therapeutically effective amount of an olaparib oxalic acid cocrystal of the invention or of administering to a patient in need thereof a therapeutic composition containing an olaparib oxalic acid cocrystal of the invention.

The term "treatment" or "treating" means any treatment of a disease, disorder, or condition in a mammal, including: preventing or protecting against the disease, disorder, or condition, that is, causing the clinical symptoms not to develop; inhibiting the disease, disorder, or condition, that is, arresting or suppressing the development of clinical symptoms; and/or relieving the disease, disorder, or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder, or condition. The term "protection" is meant to include "prophylaxis."

Another aspect of the invention relates to the use of an olaparib oxalic acid cocrystal of the invention in the treatment of diseases, disorders, and conditions discussed above. Accordingly, the invention further relates to the manufacture of a medicament for use in the treatment of such diseases, disorders, and conditions.

Pharmaceutical Compositions Containing Olaparib Oxalic Acid Cocrystals

The invention relates to pharmaceutical compositions comprising, consisting essentially, or consisting of a therapeutically effective amount of an olaparib oxalic acid cocrystal according to the invention and a pharmaceutically acceptable carrier (also known as a pharmaceutically acceptable excipient). As mentioned above, these pharmaceutical compositions are therapeutically useful to treat or prevent disorders such as those discussed above. A pharmaceutical composition of the invention may be a solid dosage form, or a liquid formulation made with an olaparib oxalic acid cocrystal of the invention.

A pharmaceutical composition of the invention may be in any pharmaceutical form which contains an olaparib oxalic acid cocrystal according to the invention. The pharmaceutical composition may be, for example, a tablet, a capsule, an oral solution, an injectable composition, a topical composition, an inhalable composition, or a transdermal composition. Liquid pharmaceutical compositions may be prepared using an olaparib oxalic acid cocrystal of the invention and represent a particular embodiment of the invention. For a liquid pharmaceutical composition, the olaparib oxalic acid cocrystal may be dissolved in a solvent, e.g. water, at the time and point of care.

The pharmaceutical compositions generally contain, for example, about 0.1% to about 99.9% by weight of an olaparib oxalic acid cocrystal of the invention, for example, about 0.5% to about 99% by weight of an olaparib oxalic acid cocrystal of the invention and, for example, 99.5% to 0.5% by weight of at least one suitable pharmaceutical excipient or solvent. In one embodiment, the composition may be between about 5% and about 75% by weight of an olaparib oxalic acid cocrystal of the invention with the rest being at least one suitable pharmaceutical excipient, solvent, or at least one other adjuvant, as discussed below.

A "therapeutically effective amount of an olaparib oxalic acid cocrystal according to the invention" is that which correlates to a therapeutic effect and may for example, be about 5 mg-about 2,000 mg, about 50 mg-about 1500 mg, about 100 mg-about 1000 mg, about 250 mg-about 750 mg, or about 500 mg. The actual amount required for treatment of any particular disease, disorder, or condition for any particular patient may depend upon a variety of factors including, for example, the particular disease, disorder, or condition being treated; the disease state being treated and its severity; the specific pharmaceutical composition employed; the age, body weight, general health, sex, and diet of the patient; the mode of administration; the time of administration; the route of administration; the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one containing an olaparib oxalic acid cocrystal of the invention, a carrier should be chosen that maintains the crystalline form. In other words, the carrier should not substantially alter the olaparib oxalic acid cocrystal. Nor should the carrier be otherwise incompatible with the olaparib oxalic acid cocrystal used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, an olaparib oxalic acid cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing an olaparib oxalic acid cocrystal of the invention with, for example, suitable non-irritating excipients or carriers such as cocoa butter, polyethyleneglycol, or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes, or foams; or solutions or suspensions such as drops, as is known in the art. Compositions of the invention may be intended for topical administration, in which case the carrier may suitably comprise a solution, emulsion, ointment, or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the olaparib oxalic acid cocrystal of the invention topically to the lung. One such means could involve a dry powder inhaler formulation of respirable particles comprised of an olaparib oxalic acid cocrystal of the invention, which the patient being treated inhales. It is common for a dry powder formulation to include carrier particles, to which olaparib oxalic acid cocrystal particles can adhere to. The carrier particles may be of any acceptable pharmacologically inert material or combination of materials. For example, the carrier particles may be composed of one or more materials selected from sugar alcohols; polyols, for example sorbitol, mannitol, or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering an olaparib oxalic acid cocrystal of the invention systemically by such methods. One such means would involve an aerosol suspension of respirable particles comprised of an olaparib oxalic acid cocrystal of the invention, which the patient being treated inhales. An olaparib oxalic acid cocrystal would be absorbed into the bloodstream via the lungs in a pharmaceutically effective amount. The respirable particles can be liquid or solid, with a particle size sufficiently small to pass through the mouth and larynx upon inhalation.

Because the crystalline form of an olaparib oxalic acid cocrystal may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler, or aerosol formulations may be used. In such solid dosage forms, the active compound may be mixed with at least one inert, pharmaceutically acceptable excipient (also known as a pharmaceutically acceptable carrier).

An olaparib oxalic acid cocrystal according to the invention may also be used to formulate liquid or injectable pharmaceutical compositions. Administration of an olaparib oxalic acid cocrystal in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

The invention also relates to a method of preparing a liquid pharmaceutical composition comprising the step of dissolving an olaparib oxalic acid cocrystal according to the invention in a pharmaceutically acceptable solvent and to liquid pharmaceutical compositions prepared according to that method. As discussed above, liquid pharmaceutical compositions of the invention may be administered orally, parenterally (including by inhalation), and intravenously.

EXAMPLES

The following analytical methods were used to characterize the olaparib oxalic acid cocrystals of the invention:

Bruker D2 X-Ray Powder Diffraction Characterisation: X-ray powder diffraction patterns for the samples were acquired on a Bruker 2nd Gen D2-Phaser diffractometer using CuKα radiation (30V, 10 mA), 0-20 goniometer, V4 receiving slits, a Ge monochromator, and a Lynxeye detector. The instrument is performance checked using a certified Corundum standard (NIST 1976). The data were collected at ambient temperature over an angular range of 2° to 35°2θ (using a step size of 0.05°2θ and a step time of 2.0 seconds) or an angular range of 2° to 42°2θ (using a step size of 0.025°2θ and a step time of 5.0 seconds). Samples run under ambient conditions were prepared as flat plate specimens using powder as received without grinding. Approximately 20 mg of the sample was gently packed into sample holder and all samples were analysed using Diffrac Plus EVA v4.2.0.14

Thermal Analysis—Differential Scanning calorimetry (DSC): DSC data were collected on a PerkinElmer Pyris 4000 DSC equipped with a 45-position sample holder. The instrument was verified for energy and temperature calibration using certified indium. A predefined amount of the sample, 0.5-3.0 mg, was placed in a pin holed aluminium pan and heated at 20° C.·min$^{-1}$ from 30 to 350° C. A purge of dry nitrogen at 60 ml·min$^{-1}$ was maintained over the sample. The instrument control, data acquisition, and analysis were performed with Pyris Software v9.0.1.0203.

Thermo-Gravimetric Analysis (TGA): TGA data was collected on a Perkin Elmer TGA 4000 system. The calibration for the energy and temperature was carried out using certified indium. Typically 2-5 mg of each sample was heated at 20° C./min in an atmosphere of Nitrogen maintained at 20 ml/min. The instrument control software was Perkin Elmer Pryis Thermal Analysis v11.1.1.0492. All data analysis was performed using Pyris Thermal Analysis software v13.3.1.0014.

Gravimetric Vapor Isotherm (GVS) Analysis: Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min$^{-1}$. The instrument was verified for relative humidity content by measuring three calibrated Rotronic salt solutions (10-50-88%). The weight change of the sample was monitored as a function of humidity by a microbalance (accuracy +/−0.005 mg). A defined amount of sample was placed in a tared mesh stainless steel basket under ambient conditions. The sample was held at 50% RH for ~60 minutes and then the initial desorption cycle was initiated. A full experimental cycle typically consisted of three scans (desorption, sorption and desorption) at a constant temperature (25° C.) and 10% RH intervals over a 0-90% range (60 minutes for each humidity level). Data analysis was performed in Microsoft Excel.

Example 1: 2:3 Olaparib Oxalic Acid Cocrystal 1.1 Preparation of the 2:3 Olaparib Oxalic Acid Cocrystal The batch of 2:3 Olaparib Oxalic Acid Cocrystal used for characterisation was prepared as follows:

Olaparib (169 mg, 0.39 mmol) and Oxalic Acid (86 mg, 0.96 mmol) were placed in a glass vial and 1.5 ml of nitromethane and 1.5 ml of nitromethane saturated with oxalic acid was added. The resulting slurry was placed in a shaker and matured for 2 days (room temperature to 50° C. on an 8 hour cycle, (heating to 50° C. for 4 hours and then cooling to RT for a further 4 hours). The product was then filtered under vacuum and dried in-vacuo at 40° C. for 4 hrs.

1.2 XRPD Characterisation of the 2:3 Olaparib Oxalic Acid Cocrystal

The experimental XRPD pattern of the 2:3 Olaparib Oxalic Acid Cocrystal as acquired on the Bruker 2nd Gen D2-Phaser diffractometer is shown in FIG. 1. Table 1 lists the angles, °2θ±0.2°2θ, and d value of the peaks identified in the experimental XRPD pattern of FIG. 1. The entire list of peaks or corresponding d values, or a subset thereof, may be sufficient to characterize the cocrystal, as well as by an XRPD pattern substantially similar to FIG. 1. For example, the cocrystal may be characterized by at least two, at least three, at least four, at least five, at least six, at least seven, or all of the peaks selected from the peaks at 10.9, 12.0, 13.7, 16.1, 17.0, 19.1, 19.8, and 20.7 °2θ±0.2°2θ.

TABLE 1

| Angle °2θ ± 0.2 °2θ | d value Angstrom | Intensity % |
|---|---|---|
| 5.8 | 15.31 | 11.5% |
| 5.9 | 14.92 | 9.9% |
| 7.8 | 11.32 | 4.6% |
| 10.2 | 8.67 | 9.3% |
| 10.9 | 8.10 | 78.9% |
| 12.0 | 7.34 | 81.7% |
| 12.0 | 7.34 | 81.7% |
| 13.7 | 6.44 | 21.3% |
| 15.8 | 5.60 | 31.7% |
| 16.1 | 5.49 | 87.2% |
| 17.0 | 5.22 | 54.4% |
| 17.5 | 5.07 | 13.3% |
| 17.8 | 4.98 | 31.3% |
| 18.2 | 4.87 | 61.7% |
| 18.5 | 4.78 | 64.1% |
| 19.1 | 4.64 | 28.8% |
| 19.8 | 4.47 | 90.4% |
| 20.7 | 4.30 | 46.6% |
| 21.4 | 4.15 | 20.3% |
| 21.9 | 4.06 | 22.8% |
| 22.7 | 3.91 | 13.4% |
| 23.3 | 3.82 | 42.5% |
| 23.7 | 3.75 | 27.9% |
| 24.4 | 3.64 | 55.8% |

TABLE 1-continued

| Angle °2θ ± 0.2 °2θ | d value Angstrom | Intensity % |
|---|---|---|
| 25.8 | 3.46 | 9.1% |
| 26.2 | 3.40 | 13.1% |
| 27.2 | 3.28 | 100.0% |
| 27.7 | 3.22 | 58.4% |
| 31.6 | 2.83 | 12.5% |
| 32.2 | 2.78 | 9.5% |
| 32.7 | 2.73 | 12.6% |
| 33.7 | 2.66 | 24.4% |
| 34.4 | 2.60 | 13.7% |
| 35.7 | 2.51 | 10.0% |
| 36.8 | 2.44 | 15.1% |
| 37.8 | 2.38 | 12.6% |
| 38.3 | 2.35 | 8.6% |
| 39.0 | 2.31 | 9.1% |
| 39.6 | 2.27 | 5.2% |

1.3 DSC of the 2:3 Olaparib Oxalic Acid Cocrystal

Figure 2:
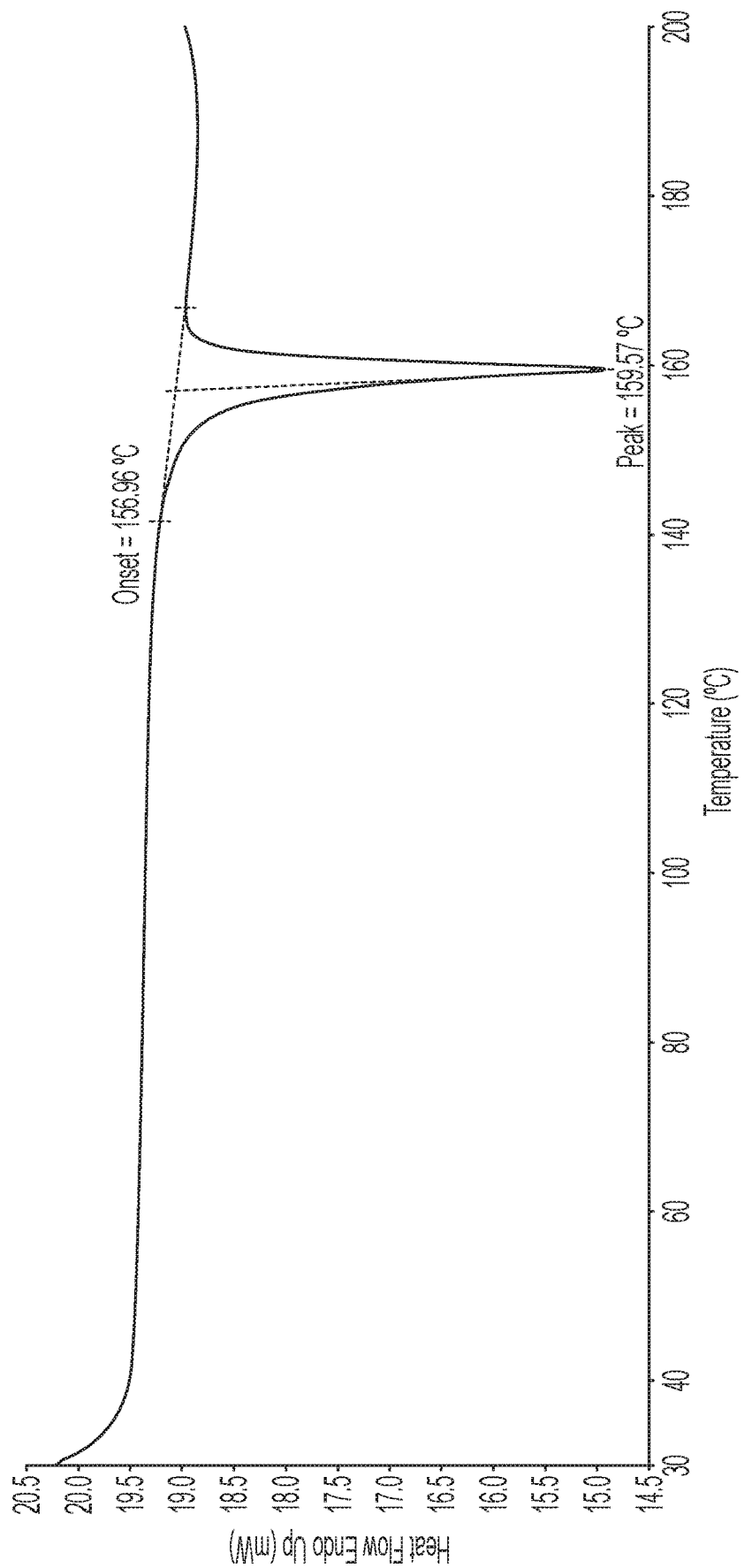
FIG. 2 shows a DSC trace for the 2:3 olaparib oxalic acid cocrystal.

The differential scanning calorimetry (DSC) trace of the 2:3 Olaparib Oxalic Acid Cocrystal, FIG. 2, shows a single endotherm with a peak maximum of 159.6° C.

1.4 TGA of the 2:3 Olaparib Oxalic Acid Cocrystal

Figure 3:
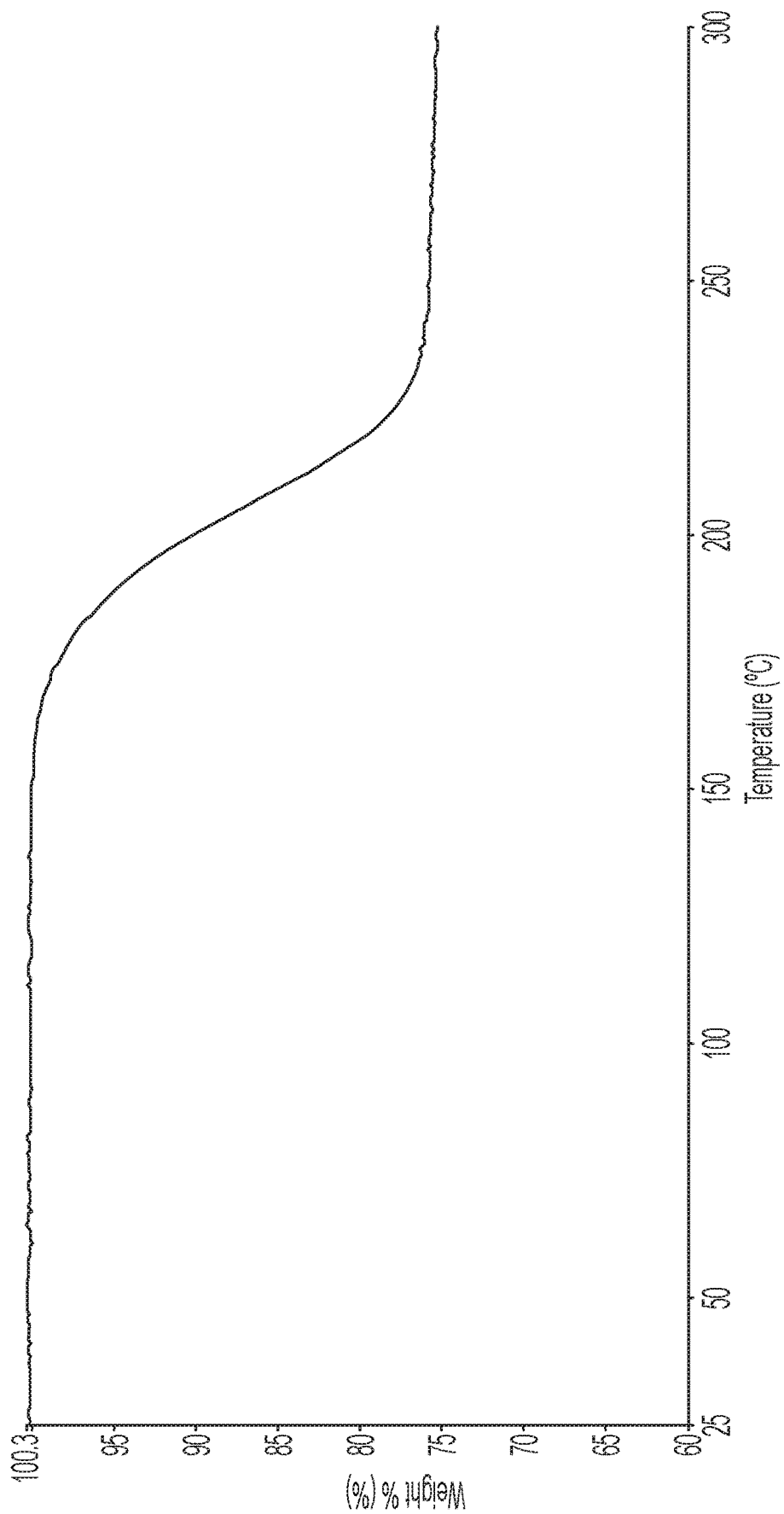
FIG. 3 shows a TGA trace for the 2:3 olaparib oxalic acid cocrystal.

In the thermogravimetric analysis (TGA) trace of the 2:3 Olaparib Oxalic Acid Cocrystal, FIG. 3, it can be seen that there is a 23.7% weight loss in the temperature range of ~155-245° C., which corresponds to the loss of 1.5 moles of oxalic acid. This confirms that the cocrystal has 2:3 olaparib:oxalic acid stoichiometry.

Figure 4:
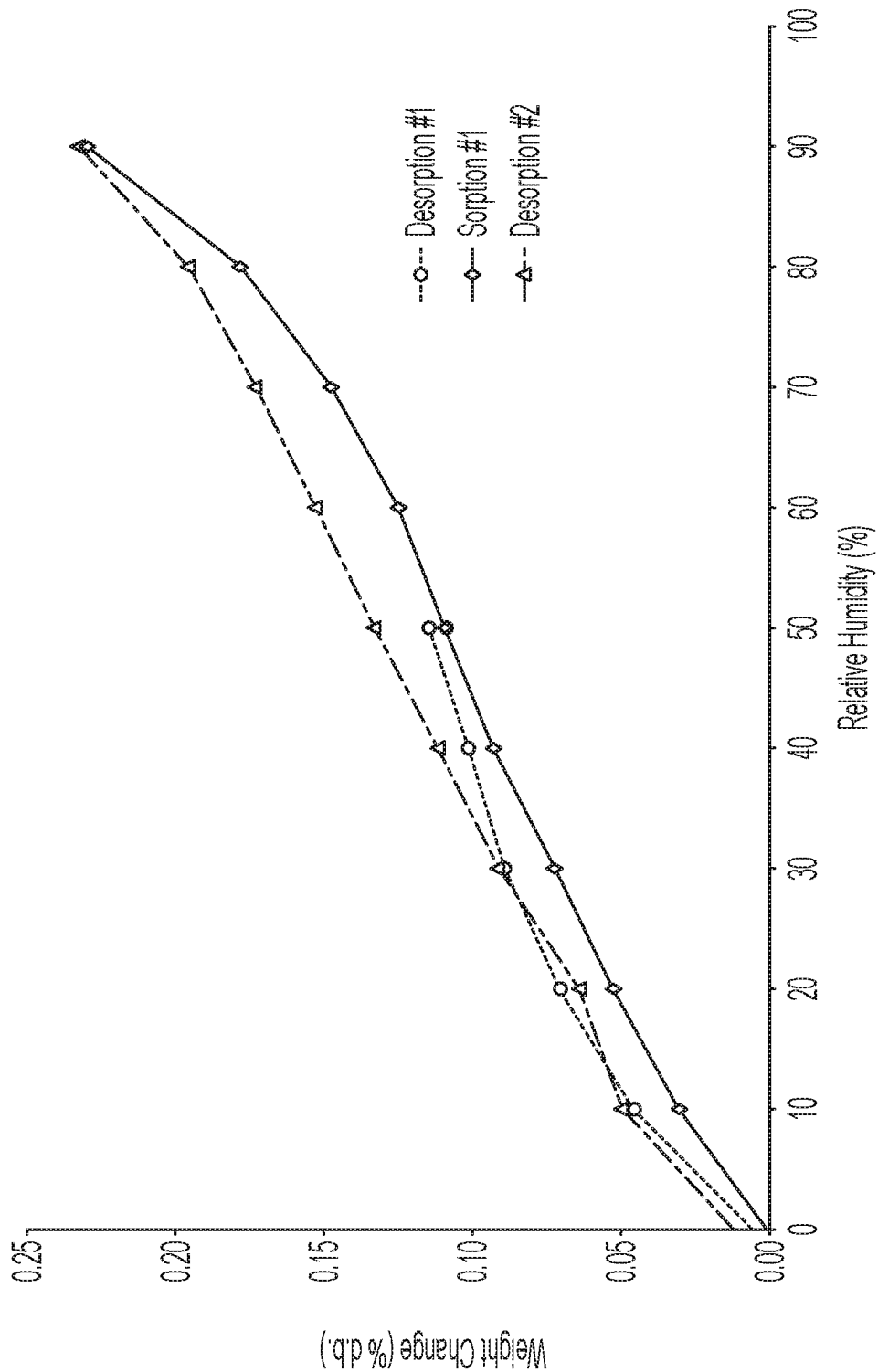
FIG. 4 shows a GVS isotherm graph for the 2:3 olaparib oxalic acid cocrystal.

1.5 Gravimetric Vapour Sorption (GVS) Analysis of the 2:3 Olaparib Oxalic Acid Cocrystal The moisture sorption isotherm graph obtained for the 2:3 Olaparib Oxalic Acid Cocrystal is shown in FIG. 4. The cocrystal was found to reversibly adsorb 0.23% w/w across the 0-90% relative humidity range at 25° C. under nitrogen. XRPD analysis at both 0% RH and 90% RH post GVS analysis confirmed that the cocrystal was unchanged. This shows that the cocrystal in not hygroscopic and does not show any polymorphic form conversion or hydrate formation under raised relative humidity levels.

Example 2: 1:1 Olaparib Oxalic Acid Cocrystal 2.1 Preparation of the 1:1 Olaparib Oxalic Acid Cocrystal The batch of 1:1 Olaparib Oxalic Acid Cocrystal used for characterisation was prepared as follows:

Olaparib (165 mg, 0.34 mmol) and oxalic acid (34 mg, 0.34 mmol) were milled together with nitromethane (3 drops) for 4×15 minutes at 30 Hz in a Retsch M M400 ball mill. The product was dried under ambient conditions overnight and then in vacuo at 40° C. for 1 hr.

2.2 XRPD Characterisation of the 1:1 Olaparib Oxalic Acid Cocrystal

Figure 5:
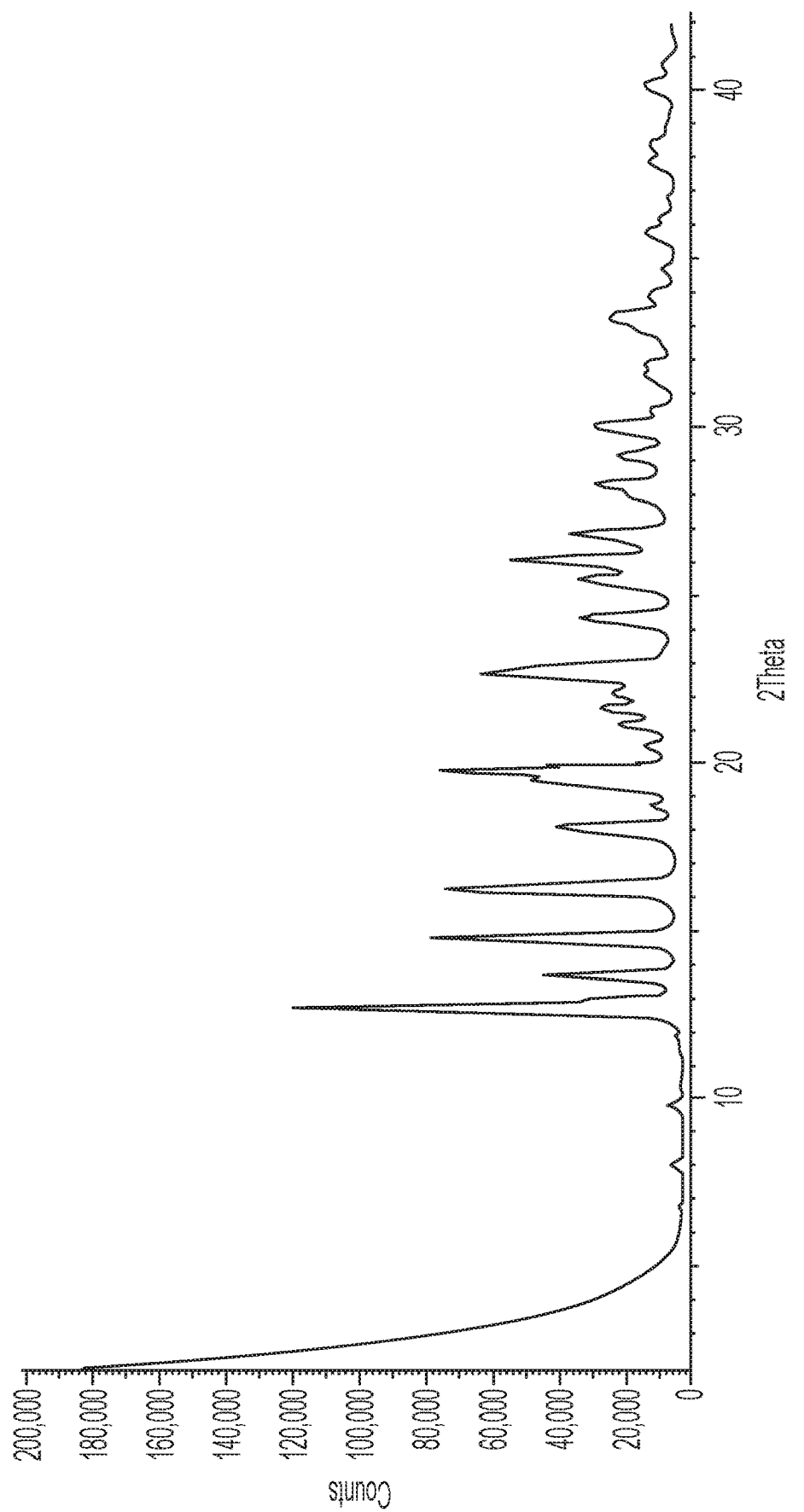
FIG. 5 shows an XRPD diagram of the 1:1 olaparib oxalic acid cocrystal.

The experimental XRPD pattern of the 1:1 Olaparib Oxalic Acid Cocrystal as acquired on the Bruker 2nd Gen D2-Phaser diffractometer is shown in FIG. 5. Table 2 lists the angles, °2θ±0.2°2θ, and d value of the peaks identified in the experimental XRPD pattern of FIG. 5. The entire list of peaks or corresponding d values, or a subset thereof, may be sufficient to characterize the cocrystal, as well as by an XRPD pattern substantially similar to FIG. 5. For example, the cocrystal may be characterized by at least two, at least three, at least four, at least five, at least six, or all of the peaks selected from the peaks at 12.7, 13.7, 14.8, 16.2, 18.1, 22.6, and 24.3 °2θ±0.2°2θ.

TABLE 2

| Angle °2θ ± 0.2 °2θ | d value Angstrom | Intensity % |
|---|---|---|
| 8.0 | 10.98 | 2.90% |
| 9.8 | 9.00 | 3.8% |
| 12.7 | 6.96 | 100.0% |
| 13.7 | 6.48 | 34.9% |
| 14.8 | 5.99 | 63.6% |
| 16.2 | 5.45 | 59.5% |
| 18.1 | 4.90 | 30.2% |
| 18.7 | 4.74 | 5.4% |
| 19.5 | 4.55 | 36.5% |
| 19.8 | 4.49 | 59.9% |
| 20.5 | 4.33 | 6.3% |
| 21.1 | 4.20 | 13.1% |
| 21.6 | 4.11 | 18.2% |
| 22.1 | 4.03 | 14.7% |
| 22.6 | 3.92 | 48.6% |
| 24.3 | 3.66 | 23.0% |
| 25.5 | 3.50 | 23.0% |
| 26.0 | 3.42 | 41.4% |
| 26.8 | 3.32 | 25.9% |
| 27.9 | 3.19 | 11.1% |
| 28.3 | 3.15 | 19.5% |
| 29.1 | 3.07 | 13.5% |
| 30.0 | 2.97 | 19.9% |
| 30.5 | 2.93 | 5.7% |
| 31.6 | 2.83 | 6.9% |
| 31.8 | 2.81 | 7.0% |
| 33.2 | 2.70 | 16.0% |
| 33.9 | 2.64 | 5.9% |
| 34.7 | 2.59 | 2.8% |
| 35.8 | 2.51 | 7.4% |
| 36.1 | 2.48 | 3.9% |
| 37.9 | 2.37 | 6.3% |
| 38.4 | 2.34 | 6.2% |
| 40.1 | 2.25 | 7.8% |
| 40.8 | 2.21 | 3.4% |

2.3 DSC of the 1:1 Olaparib Oxalic Acid Cocrystal

Figure 6:
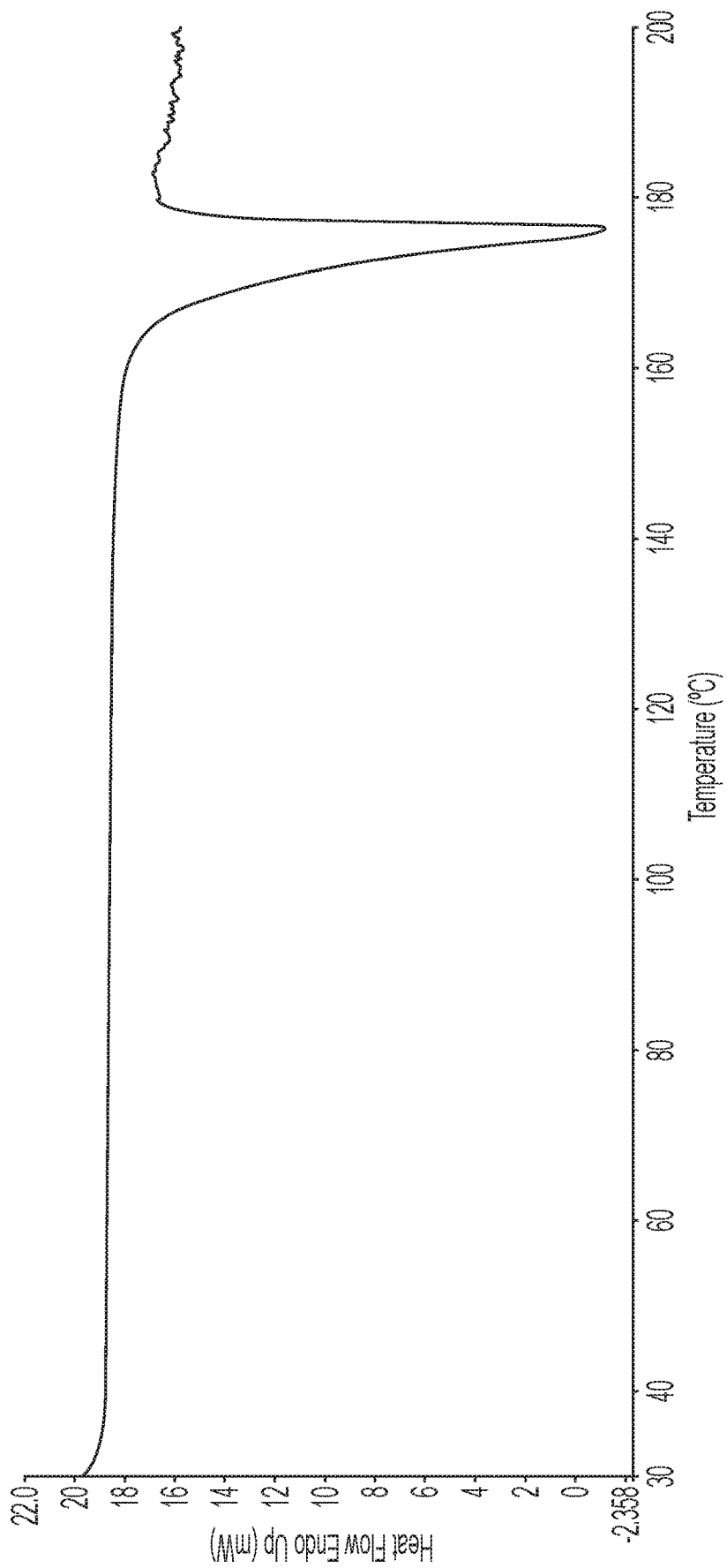
FIG. 6 shows a DSC trace for the 1:1 olaparib oxalic acid cocrystal.

The differential scanning calorimetry (DSC) trace of the 1:1 Olaparib Oxalic Acid Cocrystal, FIG. 6, shows a single endotherm with a peak maximum of 176.4° C.

2.4 TGA of the 1:1 Olaparib Oxalic Acid Cocrystal

Figure 7:
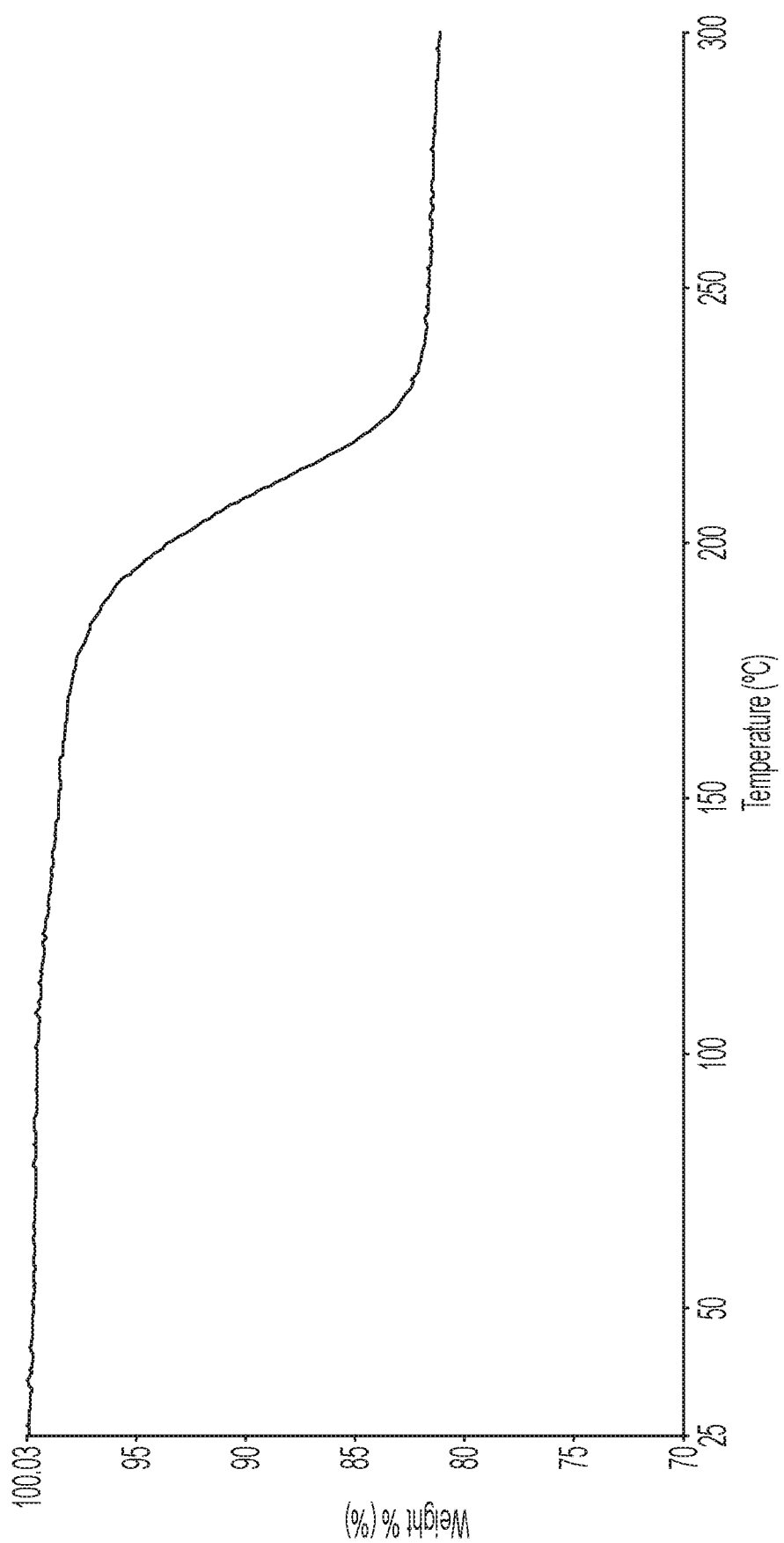
FIG. 7 shows a TGA trace for the 1:1 olaparib oxalic acid cocrystal.

In the thermogravimetric analysis (TGA) trace of the 1:1 Olaparib Oxalic Acid Cocrystal, FIG. 7, it can be seen that there is a 17.1% weight loss, which corresponds to the loss of 1 mole of oxalic acid. This shows that the cocrystal has 1:1 olaparib:oxalic acid stoichiometry.

Example 3: 2:1 Olaparib Oxalic Acid Cocrystal 3.1 Preparation of the 2:1 Olaparib Oxalic Acid Cocrystal The batch of 2:1 Olaparib Oxalic Acid Cocrystal used for characterisation was prepared as follows:

Olaparib (146 mg, 0.34 mmol) and oxalic acid (15 mg, 0.17 mmol) were milled together with isobutyl acetate (3 drops) for 4×15 minutes at 30 Hz in a Retsch MM400 ball mill. The product was dried under ambient conditions overnight and then in vacuo at 40° C. for 1 hr.

3.2 XRPD Characterisation of the 2:1 Olaparib Oxalic Acid Cocrystal

Figure 8:
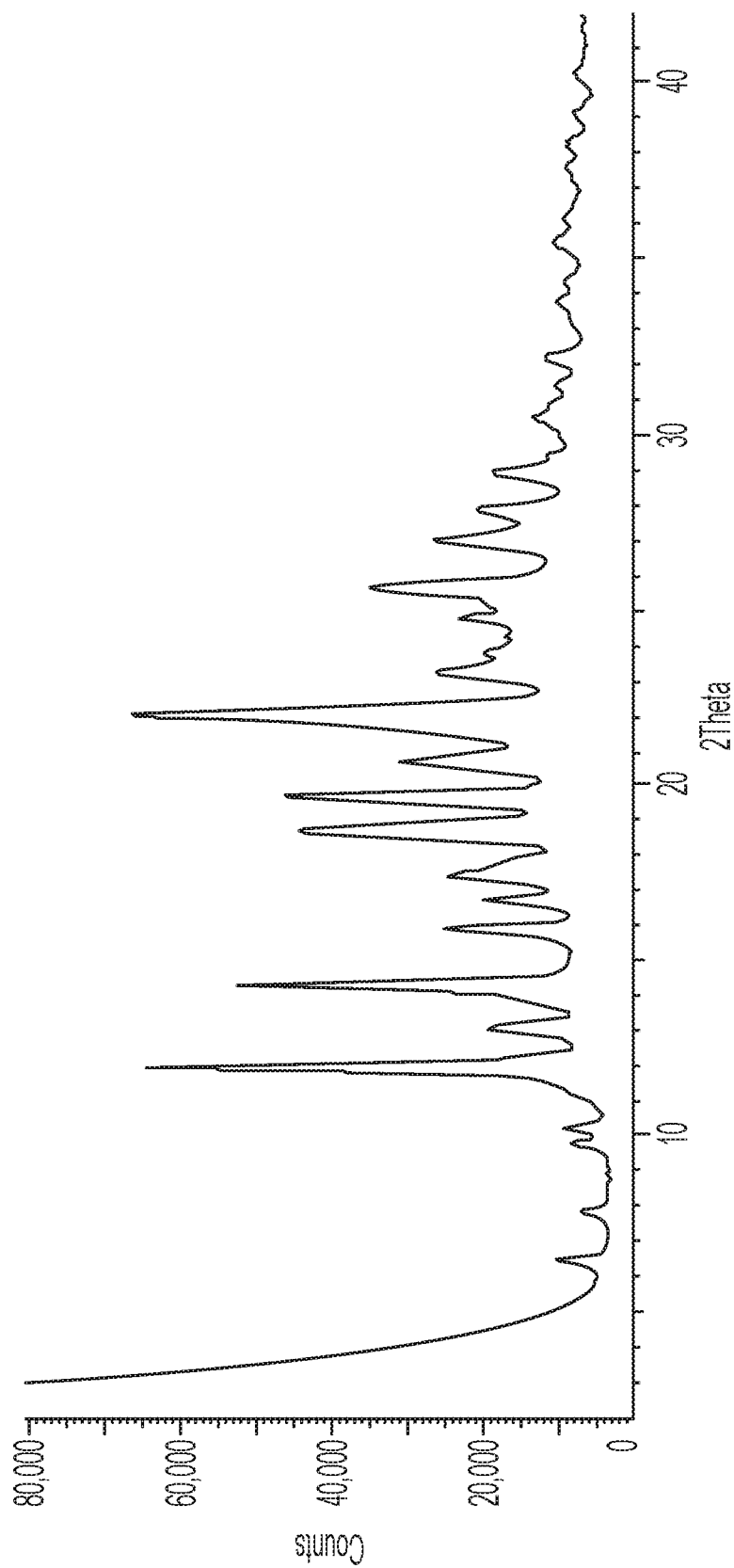
FIG. 8 shows an XRPD diagram of the 2:1 olaparib oxalic acid cocrystal.

The experimental XRPD pattern of the 2:1 Olaparib Oxalic Acid Cocrystal as acquired on the Bruker 2nd Gen D2-Phaser diffractometer is shown in FIG. 8. Table 3 lists the angles, °2θ±0.2°2θ, and d value of the peaks identified in the experimental XRPD pattern of FIG. 8. The entire list of peaks or corresponding d values, or a subset thereof, may be sufficient to characterize the cocrystal, as well as by an XRPD pattern substantially similar to FIG. 8. For example, the cocrystal may be characterized by at least two, at least three, at least four, at least five, at least six, at least seven, or all of the peaks selected from the peaks at 6.5, 7.9, 12.0, 13.1, 14.3, 15.9, 18.7, and 19.7 °2θ±0.2°2θ.

TABLE 3

| Angle °2θ ± 0.2 °2θ | d value Angstrom | Intensity % |
|---|---|---|
| 6.5 | 13.67 | 9.2% |
| 7.9 | 11.22 | 5.4% |
| 9.8 | 9.02 | 8.2% |
| 10.2 | 8.64 | 9.2% |
| 12.0 | 7.38 | 100.0% |
| 13.1 | 6.76 | 21.5% |
| 14.3 | 6.18 | 76.5% |
| 15.9 | 5.57 | 28.1% |
| 16.7 | 5.29 | 18.6% |
| 17.4 | 5.08 | 25.6% |
| 17.9 | 4.96 | 11.5% |
| 18.7 | 4.74 | 58.0% |
| 19.7 | 4.50 | 61.5% |
| 20.7 | 4.29 | 34.4% |
| 22.0 | 4.03 | 94.3% |
| 23.2 | 3.83 | 26.4% |
| 23.8 | 3.74 | 15.4% |
| 24.8 | 3.59 | 21.8% |
| 25.7 | 3.47 | 41.2% |
| 27.0 | 3.30 | 28.1% |
| 27.8 | 3.20 | 18.6% |
| 28.9 | 3.08 | 15.9% |
| 29.4 | 3.04 | 4.3% |
| 30.5 | 2.93 | 7.9% |
| 32.2 | 2.78 | 11.3% |

3.3 DSC of the 2:1 Olaparib Oxalic Acid Cocrystal

Figure 9:
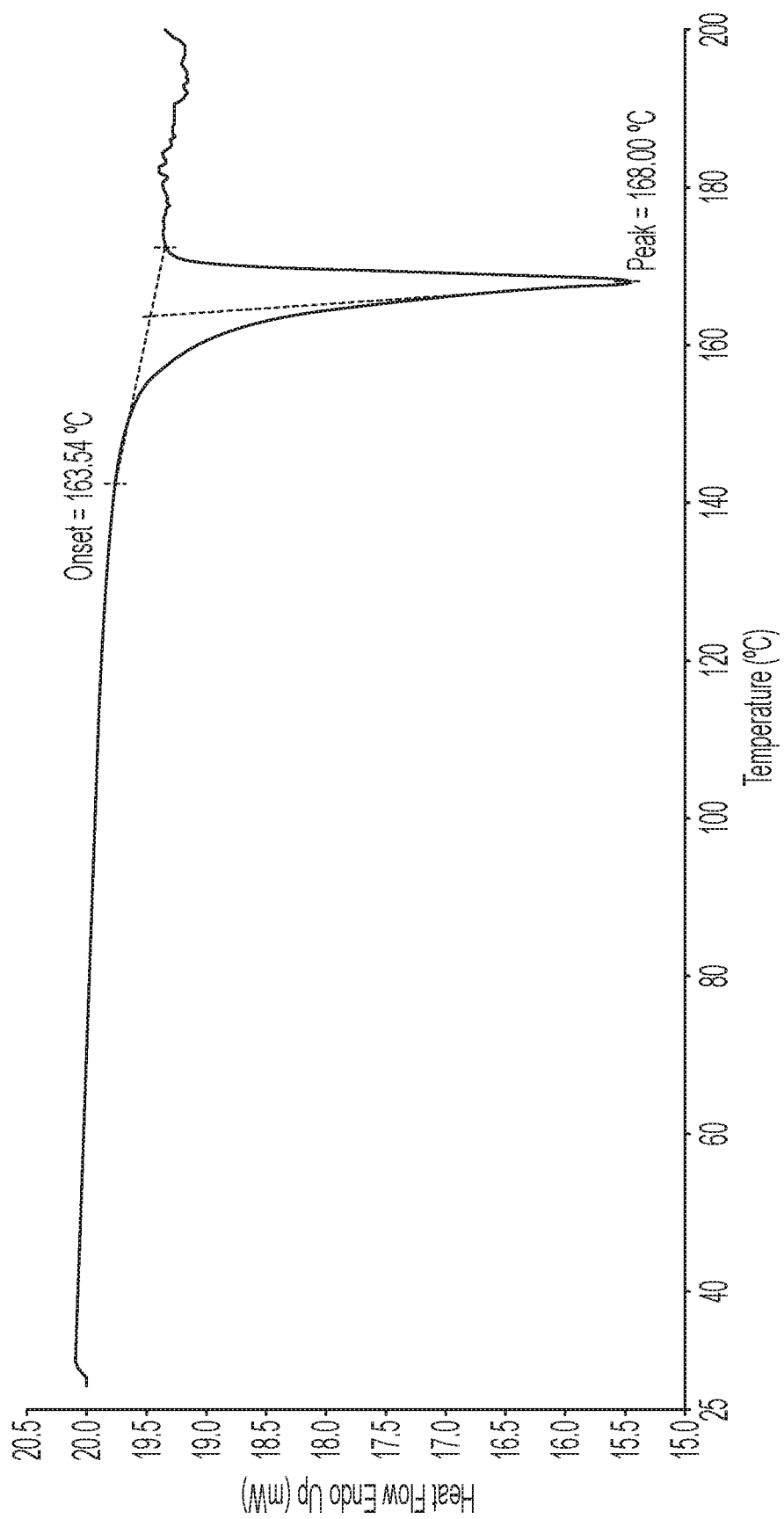
FIG. 9 shows a DSC trace for the 2:1 olaparib oxalic acid cocrystal.

The differential scanning calorimetry (DSC) trace of the 2:1 Olaparib Oxalic Acid Cocrystal, FIG. 9, shows a single endotherm with a peak maximum of 168.0° C.

3.3 TGA of the 2:1 Olaparib Oxalic Acid Cocrystal

Figure 10:
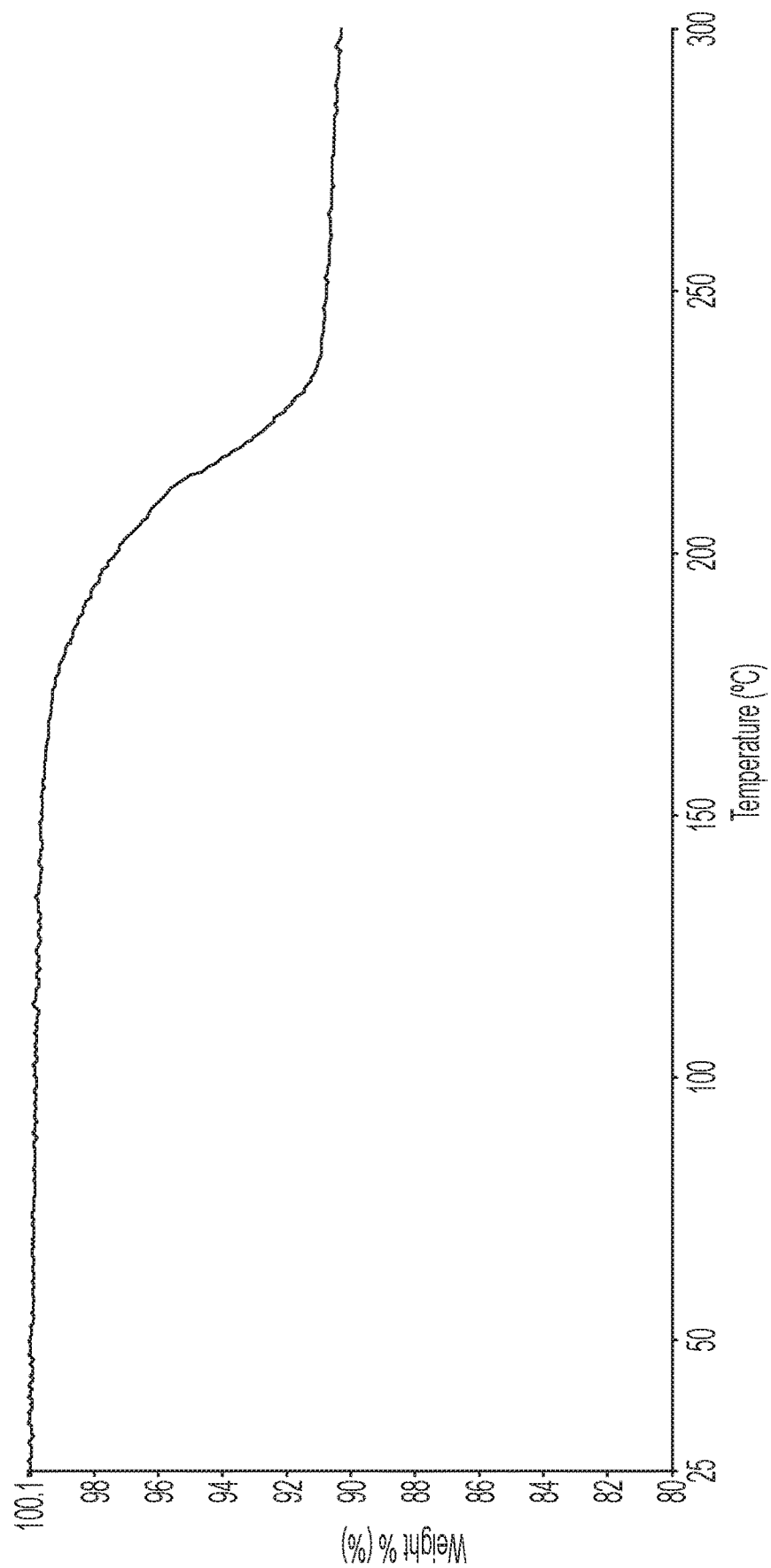
FIG. 10 shows a TGA trace for the 2:1 olaparib oxalic acid cocrystal.

In the thermogravimetric analysis (TGA) trace of the 2:1 Olaparib Oxalic Acid Cocrystal, FIG. 10, it can be seen that there is a 9.4% weight loss, which corresponds to the loss of 1 mole of oxalic acid. This shows that the cocrystal has 2:1 olaparib:oxalic acid stoichiometry.

Figure 11:
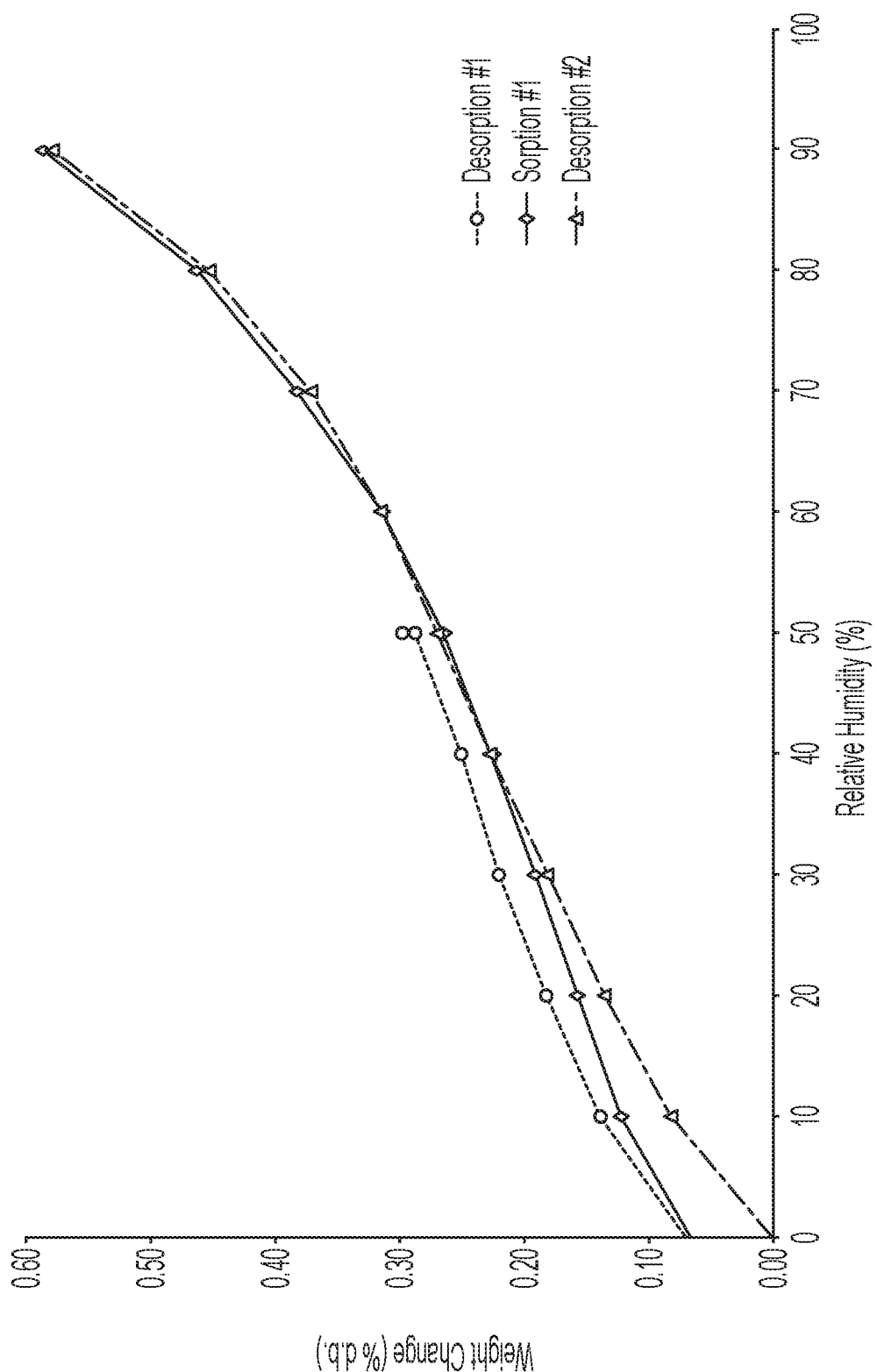
FIG. 11 shows a GVS isotherm graph for the 2:1 olaparib oxalic acid cocrystal.

3.4 Gravimetric Vapour Sorption (GVS) Analysis of the 2:1 Olaparib Oxalic Acid Cocrystal The moisture sorption isotherm graph obtained for the 2:1 Olaparib Oxalic Acid Cocrystal Form A is shown in FIG. 11. The cocrystal was found to reversibly adsorb 0.59% w/w across the 0-90% relative humidity range at 25° C. under nitrogen. XRPD analysis at both 0% RH and 90% RH post GVS analysis confirmed that the cocrystal was unchanged. This shows that the cocrystal does not show any polymorphic form conversion or hydrate formation under raised relative humidity levels.

Example 4: Solid-State Stability Study for the Olaparib Oxalic Acid Cocrystals

A study was carried out to examine the physical stability of the olaparib oxalic acid cocrystals with respect to solid form conversion or signs of decomposition over time under both ambient and accelerated conditions. 50 mg each of the 2:3 olaparib oxalic acid cocrystal, 1:1 olaparib oxalic acid cocrystal, and 2:1 olaparib oxalic acid cocrystal were separately placed in a sealed container at 40° C. and 75% relative humidity and stored under these conditions for 4 months. After this time, all samples remained as white solids with no signs of deliquescence. Each sample was analysed by XRPD to observe any potential form changes and the results of the study are shown in Table 4.

TABLE 4

| | 40° C./75% RH - 4 months | |
|---|---|---|
| Cocrystal | Appearance | XRPD analysis |
| 2:3 OLAPARIB OXALIC ACID | No change | No change (as FIG. 1) |
| 1:1 OLAPARIB OXALIC ACID | No change | No change (as FIG. 5) |
| 2:1 OLAPARIB OXALIC ACID | No change | No change (as FIG. 8) |

A second stability study was carried out where 50 mg each of the 2:3 olaparib oxalic acid cocrystal, 1:1 olaparib oxalic acid cocrystal, and 2:1 olaparib oxalic acid cocrystal were separately placed in a clear glass vial which was then stored under ambient conditions for 6 months. After this time, all the cocrystals remained as white solids with no signs of colour change. Each sample was analysed by XRPD to observe any potential form changes and the results of the study are shown in Table 5.

TABLE 5

| | Ambient Conditions - 6 months | |
|---|---|---|
| Cocrystal | Appearance | XRPD analysis |
| 1:1 OLAPARIB OXALIC ACID | No change | No change (as FIG. 1) |
| 2:1 OLAPARIB OXALIC ACID | No change | No change (as FIG. 5) |
| 2:1 OLAPARIB OXALIC ACID | No change | No change (as FIG. 8) |

It can be seen from Tables 4 and 5 that after 4 months storage under accelerated conditions and 6 months storage under ambient conditions all of the cocrystals retained their original crystalline form and that none of the olaparib oxalic acid cocrystals of this invention undergo solid form conversion or dissociation under these conditions. The 2:3 olaparib oxalic acid cocrystal, the 1:1 olaparib oxalic acid cocrystal, and the 2:1 olaparib oxalic acid cocrystal were found to be stable to polymorph conversion or hydrate formation when stored for long periods of time.

Example 5: Dissolution Studies

For BCS class IV drugs, such as olaparib, where both solubility and permeability are limited, the rate of dissolution of the drug form used can be the controlling factor in the overall absorption and thus the bioavailability of a drug. This becomes even more influential as the dose of a drug increases. Given the high dose of olaparib needed in its current marketed indications it is likely that a high dose may be needed for use in alternative conditions, thus finding a crystalline form of olaparib that has a high dissolution rate is important. A study was, therefore, carried out to examine the rate of dissolution of the 2:3 olaparib oxalic acid cocrystal, 1:1 olaparib oxalic acid cocrystal, and 2:1 olaparib oxalic acid compared with the 1:1 olaparib urea cocrystal of CN 105753789 and the pure crystalline olaparib form A. The dissolution study was carried out using 50 ml simulated intestinal fluid (FaSSIF V2) at pH 6.5 (37° C.) using a quantity of each olaparib form equivalent to 25 mg olaparib. The dissolution study was carried out using the Pion inForm® instrument. Detection and quantification of olaparib was performed by in-situ UV-spectroscopy using a fibre-optic probe, allowing instantaneous data collection from the point of sample introduction. UV absorption data was converted to mg/ml (±0.2 mg/ml) using a previously determined pH dependent molar extinction coefficients to quantitate the amount of dissolved drug.

Figure 12:
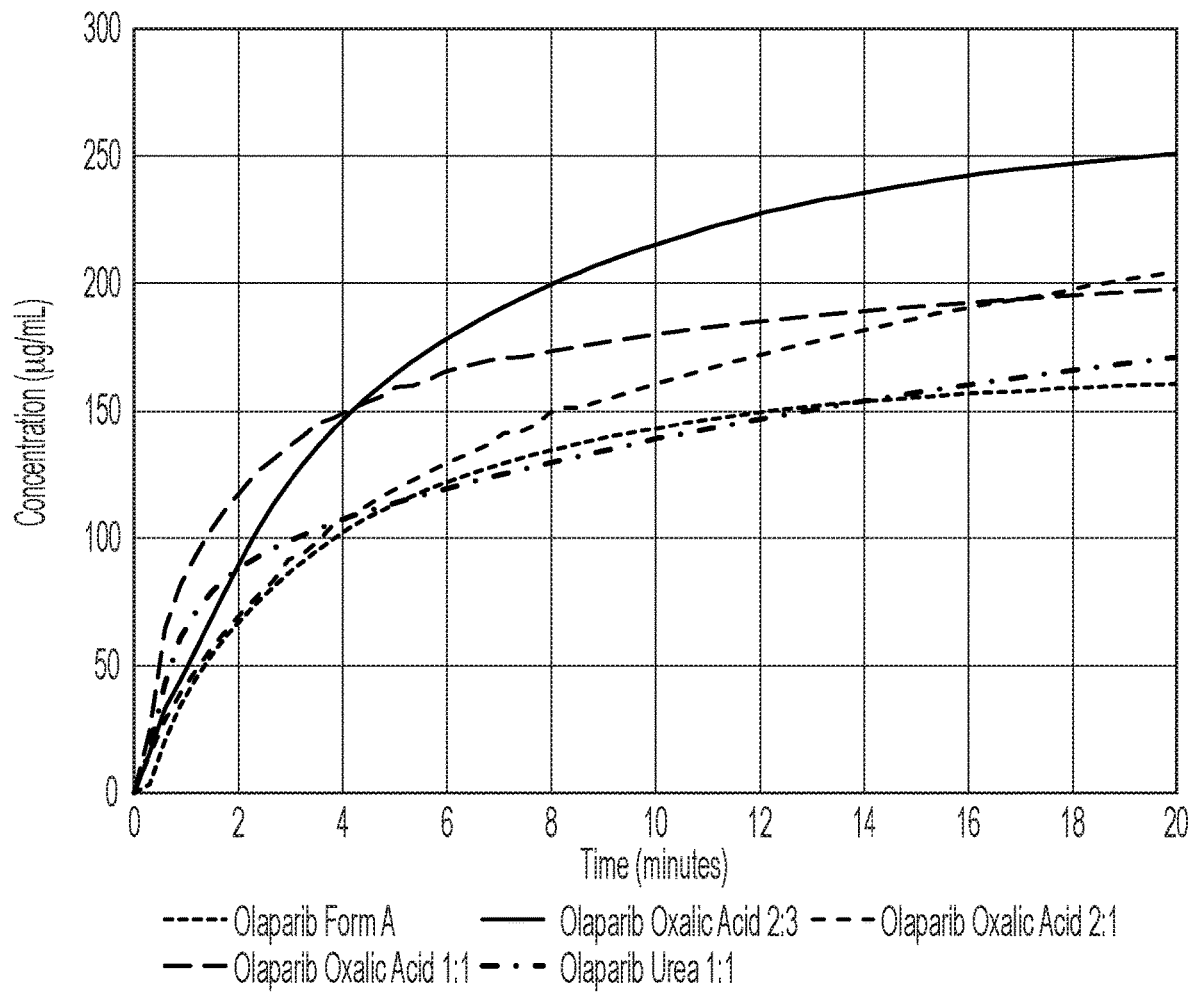
FIG. 12 depicts the dissolution profiles for the 2:3 olaparib oxalic acid cocrystal, the 1:1 olaparib oxalic acid cocrystal, the 2:1 olaparib oxalic acid cocrystal, the 1:1 olaparib urea cocrystal, and crystalline olaparib form A in FaSSIF (V2) at 37° C.

The results of the study are shown in FIG. 12. It can be seen that all of the olaparib oxalic acid cocrystals of this invention have a higher dissolution rate than the pure crystalline olaparib form A at all time points. It can also be seen that from four minutes onwards the previously disclosed 1:1 olaparib urea cocrystal only achieves the same level of dissolution as pure crystalline olaparib form A. Therefore, the olaparib oxalic acid cocrystals of this invention have a higher rate of dissolution than pure crystalline olaparib Form A and the previously described 1:1 olaparib urea cocrystal in simulated intestinal media.

The invention claimed is:

1. An olaparib oxalic acid cocrystal.

2. The olaparib oxalic acid cocrystal of claim 1 selected from the group of a 2:3 olaparib oxalic acid cocrystal, a 1:1 olaparib oxalic acid cocrystal, and a 2:1 olaparib oxalic acid cocrystal.

3. The olaparib oxalic acid cocrystal of claim 2 wherein the cocrystal is a 2:3 olaparib oxalic acid cocrystal characterized by at least one of:
   a powder X-ray diffraction pattern having at least two, at least three, at least four, at least five, at least six, at least seven, or all of the peaks selected from the peaks at 10.9, 12.0, 13.7, 16.1, 17.0, 19.1, 19.8, and 20.7 °2θ±0.2°2θ; or
   a powder X-ray diffraction pattern set forth in FIG. 1.

4. The olaparib oxalic acid cocrystal of claim 3 wherein the powder X-ray diffraction pattern has at least five of the peaks selected from the peaks at 10.9, 12.0, 13.7, 16.1, 17.0, 19.1, 19.8, and 20.7 °2θ±0.2°2θ.

5. The olaparib oxalic acid cocrystal of claim 2 wherein the cocrystal is a 1:1 olaparib oxalic acid cocrystal characterized by at least one of:
   a powder X-ray diffraction pattern having at least two, at least three, at least four, at least five, at least six, or all of the peaks selected from the peaks at 12.7, 13.7, 14.8, 16.2, 18.1, 22.6, and 24.3 °2θ±0.2°2θ; or
   a powder X-ray diffraction pattern substantially similar to set forth in FIG. 5.

6. The olaparib oxalic acid cocrystal of claim 5 wherein the powder X-ray diffraction pattern has at least four of the peaks selected from the peaks at 12.7, 13.7, 14.8, 16.2, 18.1, 22.6, and 24.3 °2θ±0.2°2θ.

7. The olaparib oxalic acid cocrystal of claim 2 wherein the cocrystal is a 2:1 olaparib oxalic acid cocrystal characterized by at least one of:
   a powder X-ray diffraction pattern having at least two, at least three, at least four, at least five, at least six, at least seven, or all of the peaks selected from the peaks at 6.5, 7.9, 12.0, 13.1, 14.3, 15.9, 18.7, and 19.7 °2θ±0.2°2θ; or
   a powder X-ray diffraction pattern set forth in FIG. 8.

8. The olaparib oxalic acid cocrystal of claim 7 wherein the powder X-ray diffraction pattern has at least five of the peaks selected from the peaks at 6.5, 7.9, 12.0, 13.1, 14.3, 15.9, 18.7, and 19.7 °2θ±0.2°2θ.

9. A pharmaceutical composition comprising the olaparib oxalic acid cocrystal of claim 1 and a pharmaceutically acceptable carrier.

10. A method of treating ovarian cancer, breast cancer, pancreatic cancer, and prostate cancer, the method comprising the step of administering to a patient in need thereof a therapeutically effective amount of the olaparib oxalic acid cocrystal according to claim 1.

11. A process for the preparation of an olaparib oxalic acid cocrystal comprising the step of slurrying a mixture of olaparib and oxalic acid in a solvent.

12. A process for the preparation of an olaparib oxalic acid cocrystal comprising the step of milling a mixture of olaparib and oxalic acid.

* * * * *